United States Patent [19]

Hatley et al.

[11] Patent Number: 5,462,518
[45] Date of Patent: Oct. 31, 1995

[54] THERAPEUTIC SPINAL TRACTION APPARATUS AND MULTIPURPOSE EXERCISE SYSTEMS AND METHODS

[76] Inventors: Charles A. Hatley; Deborah A. Atchison, both of 1232 Lighterwoods Dr., Mobile, Ala. 36695

[21] Appl. No.: 206,649

[22] Filed: Mar. 7, 1994

[51] Int. Cl.$^6$ .................................................. A61H 1/02
[52] U.S. Cl. ........................... 602/36; 482/124; 482/128
[58] Field of Search ............................... 602/32, 35, 36, 602/40; 606/241; 482/67, 121, 122, 124, 128

[56] References Cited

U.S. PATENT DOCUMENTS

| | | | |
|---|---|---|---|
| 1,722,205 | 7/1929 | Freund. | |
| 3,118,441 | 1/1964 | George | 482/122 |
| 3,394,933 | 7/1968 | Benoit | 482/67 |
| 4,715,362 | 12/1987 | Scott | 602/36 |
| 4,834,366 | 5/1989 | Hotchkiss | 482/128 |
| 5,207,626 | 5/1993 | Einhorn et al. | 482/124 |
| 5,224,924 | 7/1993 | Urso | 482/38 |

FOREIGN PATENT DOCUMENTS

| | | | |
|---|---|---|---|
| 1621927 | 1/1991 | U.S.S.R. | 602/36 |
| 1739991 | 6/1992 | U.S.S.R. | 602/36 |

Primary Examiner—Richard J. Apley
Assistant Examiner—Jeanne M. Clark
Attorney, Agent, or Firm—George L. Williamson

[57] ABSTRACT

A multipurpose method and apparatus for: a) applying continuously variable suspension traction and decompressive forces to the spine to alleviate certain types of back pain, b) stretching, elasticizing, exercising, and strengthening, the muscles which affect an individuals's spine, appearance, and posture, c) spinal manipulation and adjustment, and d) relieving pain and stress in the neck and shoulders. The apparatus, which does not restrict normal activities, utilizes spring loaded tube assemblies which are biased apart, and extend from, supports under each arm of the user to each side of an adjustable, multilayered belt adjacent the pelvis. Longitudinal adjustment of the tubes can vary the degree of traction while temporary variations can be accomplished by forcibly lowering the shoulders down into their normal position against the resistance of the compression springs. Exercising and stretching the muscles of the torso which affect the spine, posture and appearance, and to provide maximum suspension, decompression, and unloading can be accomplished by utilizing the removable handle attachments. The attachments extend from the support tubes just beneath the underarm supports, and transfers the load from the underarms to the hands, arms, and shoulders.

7 Claims, 11 Drawing Sheets

THERAPEUTIC SPINAL TRACTION APPARATUS AND MULTIPURPOSE EXERCISE SYSTEMS AND METHODS

BACKGROUND OF THE INVENTION

The present invention applies to therapeutic traction and support devices for use in applying spinal traction and for decompressing and unloading a person's back and spine to alleviate certain types of backaches. It also relates to spinal orthotic devices and more particularly to such devices for controlling body posture with or without rigidity. The present invention also applies to exercise and stretching equipment and back exercising devices having a spring load to the arms, underarms, or shoulders. The present invention further applies to devices designed to improve body posture and to improve appearance.

It is known in the art that spinal traction and stretching of the back can provide relief from certain types of back pain, particularly in the lower or lumbar region of the spine. Such stretching can have therapeutic value for certain back injuries to the thoracic and lumbar regions of the spine, as well as, certain congenital spinal maladies, e.g., scoliosis.

Large forces are brought to bear on the base of the spine (lumbo-sacral spine) when standing or seated. In treating pathologic conditions of this region it becomes necessary to support the area by stabilization. To effect this stabilization, it is necessary to control much of the thoracic spine as well.

Most braces for lower back problems do not attempt to control the thoracic spine. It is this pendulum with much of the body weight on it that creates the tremendous load on the lumbar sacral spine. Some conditions require the pelvis to have an anterior or posterior tilt.

The body may become crooked because of natural involuntary countermeasures to relieve the pain caused by a pinched nerve in the spine. Chiropractic medicine advances relief from back pain through alignment/adjustment of the spine. The adjustment generally involves a patient being aligned as a result of a snapping, or popping, of the spine induced by a chiropractor. This may temporarily relieve the pain, but does nothing for the offending musculature, and does not improve muscle tone in the required area. Usually patients are required to make repeated visits and undergo repetitive treatments. Although this approach can be helpful in some instances regarding the temporary alleviation of pain, it can also do more harm than good. The sudden snapping or cracking of the spine can cause trauma and distress to the vertebra, joints, and discs of the spine. This can lead to the need for more serious medical treatment. Because of these drawbacks, and others, chiropractic treatment is not generally accepted, advanced, or recommended by the medical community.

The medical profession advances relief from back pain from prescription muscle relaxers, injections near the affected area of the spine, bed or table traction, surgery, etc. The medical profession also prescribes repetitive physical therapy treatment that includes: electro-shock, heat pads, massage, and certain types of exercise. Medically recommended home therapy to position the spine in a neutral or balanced position includes: extensive bed rest, minimum mobility, and, occasionally, stretching exercises.

Exercise is the best way to build muscle strength and flexibility in order to maintain the proper shape of the spine. Good body mechanics and a strong, flexible back are the best defense against back injury. Improper implementation of some exercises, however, can damage the back and cause disc and vertebrae degeneration, especially in the lower back, i.e., doing sit-ups with straight-legs pull on the psoas muscles, which are attached to the lower six spinal vertebrae and the front of the legs, thereby causing the spine to be pulled out of it's balanced neutral position.

When a person is seated the weight of his or her upper body presses down on the lower back, which can cause stress and pain if this area is injured or weak. Sometimes, sitting in a vehicle, boat, or aircraft can cause considerable discomfort in that the lower back is constantly subjected to impact.

The usual approach, to spinal problems which may be alleviated by traction, is to require a patient to lie in bed with cables attached to portions of the patient's body and sand bags or other weights attached to the cables to apply tension to the patient and in order to relieve compressive forces on the patient's spine. This is, of course, a highly restrictive treatment. Other approaches include systems such as that disclosed by U.S. Pat. No. 3,167,068 wherein a patient sits in a chair with an upright lumbo-sacral traction system attached to the chair. The patient is thus free to use his or her arms while undergoing traction. However, the patient is not ambulatory and has minimal control Over the pressure applied.

Still another approach is to suspend the human body above the floor, either hanging from the feet or ankles or hanging from the underarms or rib cage area. This approach utilizes the force of gravity to stretch the lower spine. It is disclosed by U.S. Pat. No. 4,170,988 wherein the patient is suspended upside down while retained by his or her ankles. With this approach, the weight of the patient's body is used to tension the spine and thus relieve compressive forces in the spine. While the patient is suspended upside down, there is not much the patient can do. Generally, each treatment takes five (5) to ten (10) minutes and may provide the patient with sufficient relief to perform normal activities for perhaps a day or so before the treatment must be repeated. The limitations and problems with this approach are discussed by U.S. Pat. No. 4,715,362, i.e., blood tends to pool in the patient's head, increasing the risk of an aneurysm and possibly damage to the patient's eyes due to increased fluid pressure therein.

The form of apparatus for stretching or bracing which involves exerting force on two areas of the body above and below the lumbar spinal region, to force those two areas away from each other, also suffers from a number of inadequacies. Such braces are relatively bulky or can be quite uncomfortable to the wearer. In addition, the static stretching, once a brace is adjusted to exert a certain force between the two areas of attachment to the body, remains essentially constant unless and until the brace is readjusted. It is known that the cyclical stretching of the spine can be more beneficial, thus the desirability of the use of, e.g., stretching tables as noted above, which have, however, the inconveniences noted above.

Ballard, U.S. Pat. No. 3,420,230, provides the following as examples or conditions which require immobilization in a neutral position and/or unweighting or unloading of the spine, or traction: ankylosis spondylitis, dicitis, post-spinal fusion, degenerative arthritis, osteoporosis, and pathologic fractures. Some require conditions, as for example compression fractures, hyper-extension of the diseased region of the spine. Other conditions require a flexing type brace for conservative treatment of ruptured intervertebra disc, lumbo-sacral sprain, spondylolisthesis, and the like. Ballard shows a passive or inactive back brace that is worn passively and does not have compressible support members. It does not actively stretch, exercise, or condition the muscles which provides support to the spine.

Erickson, U.S. Pat. No. 2,604,889, shows the use of a device incorporating a single crutch-like underarm brace in conjunction with a waist strap for uses other than back support. Erickson does not address or suggest therapy for problems of the back or spine. Erickson teaches away from a spring-loaded underarm support because it's goal is immobilization and it is one sided, which are undesirable characteristics for back and spine therapy.

Goodley, U.S. Pat. No. 4,583,533, describes a device which exerts suspensory force on the torso in the rib cage region by way of struts which rest upon a surface on which the wearer is sitting or standing. The device only works while the struts have foundation on a suitable surface, therefore, for this reason and others, it has limited value during mobilization. It does not allow for decompression of, or therapy to, the cervical and thoracic spine, and it does not provide a system for exercising the muscles which affect the back, spine, posture, or appearance.

Scott, in U.S. Pat. No. 4,715,362 [Scott ('362)], provides a lumbo-sacral traction system to absorb shock to the spine from ambulation. Scott ('362) describes a device having an upper and lower support belt which encircles a patient adjacent to the pelvis and adjacent to the patient's upper back just beneath the arms. Support is provided by a plurality of rear mounted vertical compressible struts on both sides of the spine for absorbing shocks resulting from ambulation.

Scott ('362) teaches minimal upward lift and spinal decompression and there are no pressure release mechanisms to actively control, and/or to relieve, the amount of tension on the back. It does not allow a means to cause a posterior or anterior tilt to the pelvis which is necessary for certain conditions. Scott ('362) does not address, or provide therapy to, the thoracic or cervical spine or the muscles associated with the spine. The device has no handholds or pressure release mechanisms to control, and/or to relieve, the amount of tension on the spine. It does not exercise, stretch, or work the muscles which are responsible for holding the spine in a balanced neutral position, or the muscles responsible for posture and appearance (i.e., the back muscles, spinal erectors, abdominal, rhomboideus, latissimus dorsi, internal and external obloquies, psoas, and levator scapulae). The Scott ('362) device has the struts in the rear and does not allow the wearer to sit or lay comfortably. It does not restrict trunk flexion or bending the upper body, therefore, it provides minimal support when the wearer is forced to lean forward.

Scott, in U.S. Pat. No. 4,881,528 [Scott ('528)], addressed the sitting problem with his "spinal traction and support unit used while seated." Scott ('528) is static and is only effective while seated. Its effectiveness is further dependent upon, and affected by, the rigidity of the seating surface. As such, it has limited value when the wearer sits on a surface with deep cushioning. The Scott ('528) device does not use compressible struts and does not offer traction or tension adjustments. The device does not address, stretch, or exercise the muscles which affect the spine's balanced neutral position or the muscles which affect posture or appearance.

As shown, all of the devices shown in the prior art can only be used or worn passively. The above also demonstrates that existing apparatuses for treating back pain, and therapeutically treating back ailments, have not been altogether satisfactory. In view of the limitations and drawbacks of the prior devices and treatments, there is a need for an apparatus which: (a) applies traction to the spine, (b) decompresses and unloads the back and spine, (c) allows the wearer to safely stretch, elasticize, exercise, and strengthen the muscles which affect the problem, (d) relieves harmful stress and tension to the back, spine, and the offending muscles while also providing the user with a safe effective means to improve body posture, tone the upper body, and improve appearance, (e) permits a patient to be unrestricted while undergoing treatment.

SUMMARY OF THE INVENTION

A multipurpose apparatus and method is shown which can be used actively or inactively, which solves the problems listed above. The present invention may be used inactively as a spinal traction and support unit to redistribute upper body weight to the pelvic region, adjacent to the hips. In this manner, the apparatus gradually unloads, decompresses, and conditions the spine while relieving certain types of back pain, particularly from the thoracic and lumbo-sacral regions of the spine. When used actively, the disclosed invention applies greater decompression and unloading forces on the spine to relieve certain types of back pain and to aid the body in placing the spine in its balanced neutral position. The apparatus exercises and stretches the muscles of the torso, particularly those muscles responsible for maintaining the spine's three natural curves. This allows the present invention to alleviate back pain, aid the natural healing process, and also to prevent damage to the spine.

Certain significant advantages are provided by the present invention. In particular, it supports the spine, provides spine and muscle therapy, improves posture, tones the upper body, and provides relief from certain types of back pain. It can be used in any position as an exercise device for many muscles in the body, including back, abdominal, shoulder, obliques, and arms. Therefore, the apparatus also presents a new, safe, and effective method to attack fat in the arms, stomach, and sides.

The present invention contemplates a support belt assembly encircling a patient adjacent the patient's pelvis and upper supports which rests under the wearer's arms. The support means are held in spaced relation by spring loaded interconnected concentric support tubes that are longitudinally and laterally adjustable.

The support tubes incorporate padded underarm supports that are shaped for comfort and functionality. The support belt assembly comfortably redistributes the upper body weight evenly to the hip area.

The inner springs provide traction to the spine and resistance for exercising. The springs are interchangeable and the spring loads are variable to accommodate individuals with different upper body weights or different traction, decompression, unloading, and/or exercise requirements. A weak spring would lift a lighter person but would not support someone with a heavier upper body weight; whereas a spring necessary to lift a heavy person would remain rigid under the weight of a lighter individual.

The present invention traction's, or tensions, the spine through scapular elevation, or put another way, raising the shoulders. This is caused by the spring loaded support tubes between the lower support belt and the underarm pads. These spring loaded support tubes tend to place a force, tension, stress, or pressure between the lower support belt and the underarm pads by pushing against the two members so as to predispose or bias the two members apart. The degree of pressure, lift, and traction can be varied by adjusting the total length of the tube assemblies, which in turn increases or decreases the resistance from the spring. The greater the pressure placed on the springs, the greater the support, and traction, to the wearer.

The user can vary the degree of lift by adjusting the length of the tube assemblies or by forcibly lowering the shoulders against the resistance of the biasing means. The latter movement can be accomplished with or without use of the handle attachment. The user can use his shoulder and/or arm muscles to vary the amount of tension depending on the requirements or activity of the user. This allows for cyclical variation of the upward force exerted on the upper body, which has been shown to be beneficial.

The present invention is easy to put on and remove and is comfortable to wear. It provides the beneficial results of a suspension stretching apparatus, similar to the prior art, regardless of the wearer's activity, i.e., the wearer is not required to remain lying, seated, standing, etc., does not require attachment to a stretching bed or table, and is not required to hang the entire body right side up or upside down from a suspension apparatus as according to the prior art.

The present invention can relieve the spine of some, all, or more than all of the upper body weight. Positive lift that is greater than the upper body weight can be achieved by exerting a downward force on the biasing means that would lift more weight than would be required to lift the upper body. This hyper-stretching of the back allows the spine to safely align or seek it's balanced neutral position.

When used as an exercise device, the apparatus aids in preventing the occurrence of certain back maladies by stretching, elasticizing, exercising, and strengthening the muscles of the upper body, particularly the muscles that support the spine and maintain it's balanced neutral position.

Exercising and stretching the muscles of the upper torso and greater decompression of the spine is accomplished by scapula elevation and demotion, (repeatedly forcing the scapula down into its normal position). This movement could be considered reverse shoulder shrugs. This also exercises and stretches the muscles connected to the cervical region of the spine. The wearer can be helped in accomplishing this movement with the exercise handle attachments that transfer the pressure from the underarms to the arms and/or shoulders.

Greater shoulder elevation or hyper-extension requires greater force to lower the shoulders back into its normal position. This allows the wearer to decide the amount of resistance which best suits the wearer's needs.

The present invention does not place adverse pressure on the spine. In fact, during use, the spine is relieved even of natural loads, therefore, the present invention allows the user to exercise without fear of damage to, or pain from, the back or spine.

Exercising with the present invention attacks body fat that causes pressure on the back and affects appearance. The present invention, by decompressing the back, stretching and exercising the muscles of the torso, and burning upper body fat, also works to improve posture.

The construction, and use of the present invention, is such that body movement is permitted in all modes affecting the spine, i.e., flexion, extension, lateral bending and rotation, imparting a feeling of freedom, but against such resistance imposed by the device as to yield a physiologically desirable degree of immobilization. At the same time, lateral adjustment of the support tube assemblies on the belt, which would cause them to be forward or rear of the underarm, can cause an anterior or posterior tilt to the wearer that is beneficial in treating certain conditions of the spine.

The upward lift on the spinal cord from the present invention reverses the harmful effect of gravity and other back maladies. Decompressing and unloading the spine allows the wearer to heal quickly and naturally.

The present invention could negate bed traction for many users and provide an alternative to individuals who would reject injections near the spine, or ingestion of muscle relaxers. It would, in many cases, supplant repetitive visits for chiropractic treatment for back and neck alignment/adjustment. It could be prescribed and used by medical doctors and physical therapist.

The present invention has therapeutic value and preventive value. It can decompress and align the spine to relieve pain resulting from pinched nerves, strains, sprains, tension, stress, cramps, tense muscles, bulging discs, herniated discs, etc.

The present invention has the "relative mobility of a brace-type apparatus with the more therapeutically beneficial results of a suspension or traction type apparatus. Simultaneously, it incorporates a capability of cyclically stretching the spine. The support arms being on the sides rather than in the back as they are with the Ballard brace, or the Scott, devices, can give greater back support, if needed, when the wearer is forced to lean forward. Accordingly, a further object of the present invention is to provide a spinal orthotic device, which is comfortable, allows freedom of movement for the wearer, and yet, controls and improves body posture. The present invention does allow the wearer to have a degree of forward and backward movement associated with bending the torso at the hips or rotational movement in turning the upper torso, or a combination thereof. This allows the wearer to use the apparatus while working at a desk job, standing, lying, etc.

The springs in the support tubes can act as shock-absorbers to absorb at least a substantial portion of the vertical impact that would ordinarily be transmitted through the wearer's spine from walking or riding in a vehicle, boat, or aircraft. This is, therefore, also a prophylactic apparatus.

Examples of the more important features of the present invention have thus been summarized rather broadly so that a detailed description thereof that follows may be better understood, and in order that the contribution to the art may be better appreciated. There are, of course, additional features of the invention that will be described hereinafter.

It is a further purpose of the present invention to provide a body harness that may be easily worn and adjusted by one person and to provide a device that allows for exercise of the upper body muscles of the back, front, sides, and arms in a way that is not tedious and can be subject to a wide degree of variability.

It is an object of the present device to relieve stress and tension while encouraging mobility and arm motion and allowing the device to be non-interfering, and also to provide an exercise device that is convertible within the scope of providing back therapy via several different exercises.

For conditions that require stabilization to prevent flexion or rotation, the present invention could employ two support tube assemblies on each side of the user that would form triangles with the side section of the support belt.

One example for modifying and automating the present invention would be to make it pressure operated (pneumatic, hydraulic, etc.) and controlled by a Central Processing Unit (CPU). The wearer could regulate the variations of lifting pressures and the intervals and durations of support and lift. This would allow for infinite variations in weight and lifting pressures and would duplicate the effect of cyclical stretching and release.

These and other similar modifications of the invention will be apparent to those skilled in the art. These will become better understood hereinafter from a consideration of the specification with reference to the accompanying drawings forming a part thereof, and in which like numerals correspond to parts throughout the several views of the invention. It is the applicant's intention to cover such equivalent modifications and variations as fall within the spirit and scope of the invention.

BRIEF DESCRIPTION OF THE DRAWINGS

Other features and advantages of the present invention will become apparent with reference to the following detailed description of a preferred embodiment thereof in connection with the accompanying drawings.

DETAILED DESCRIPTION OF THE PREFERRED EMBODIMENT(S)

Figure 1:
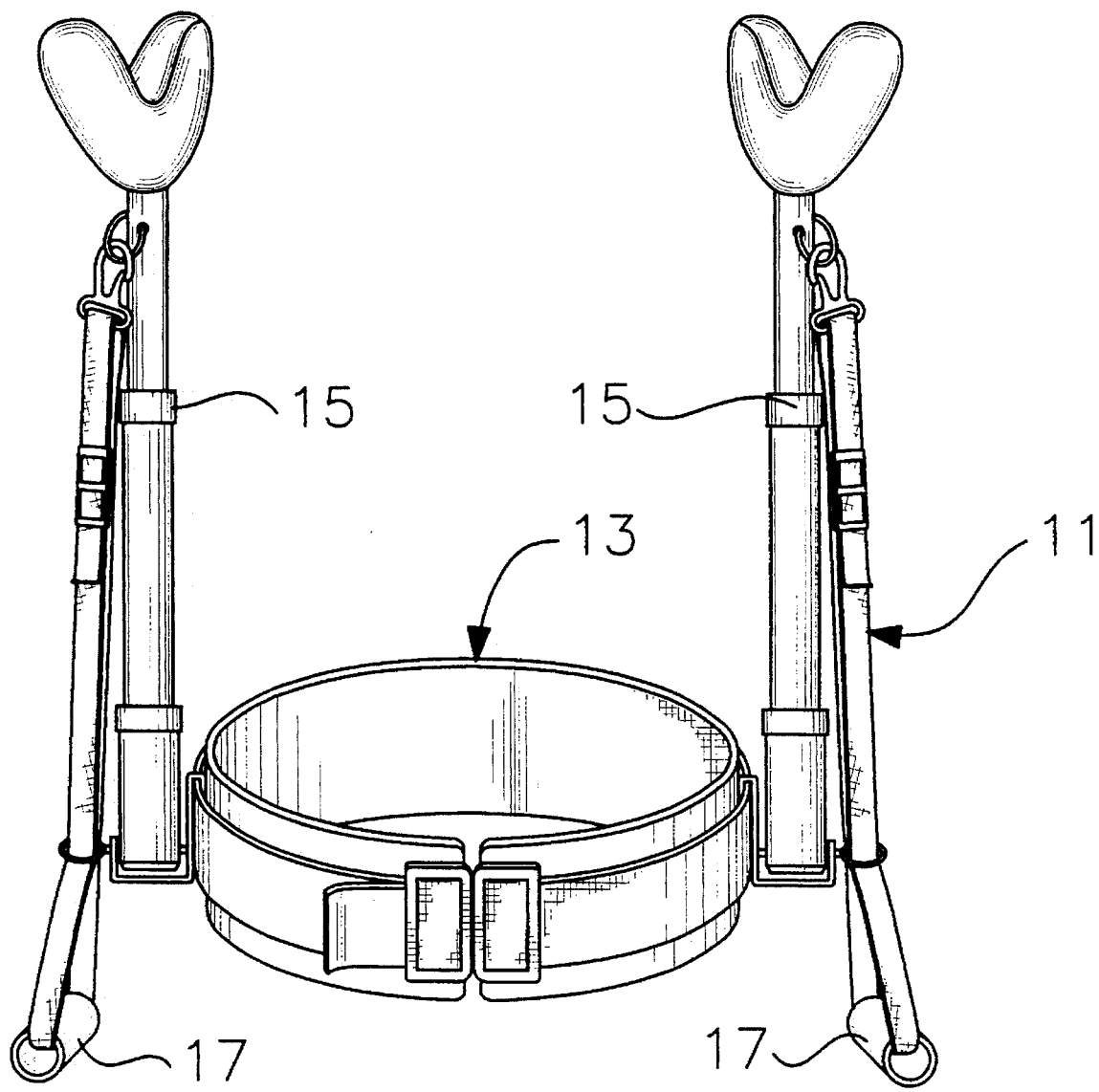
FIG. 1 is a perspective of the present invention showing the basic embodiment incorporating the detachable handle assembly.

The invention as can be seen by reference to FIG. 1, is generally at 11. The invention consists primarily of a belt means or support belt assembly 13 which encircles the user's pelvis adjacent the hips. Support belt assembly 13 bears two biased support tube assemblies or biasing means, 15, one on each side. Any reference to support tube assembly 15, applies, and is a reference, to both support tube assemblies. Handle assemblies 17 or other grip means connect to support tube assemblies 15. Any reference to handle assembly 17 is a reference to both handle assemblies.

Figure 2:
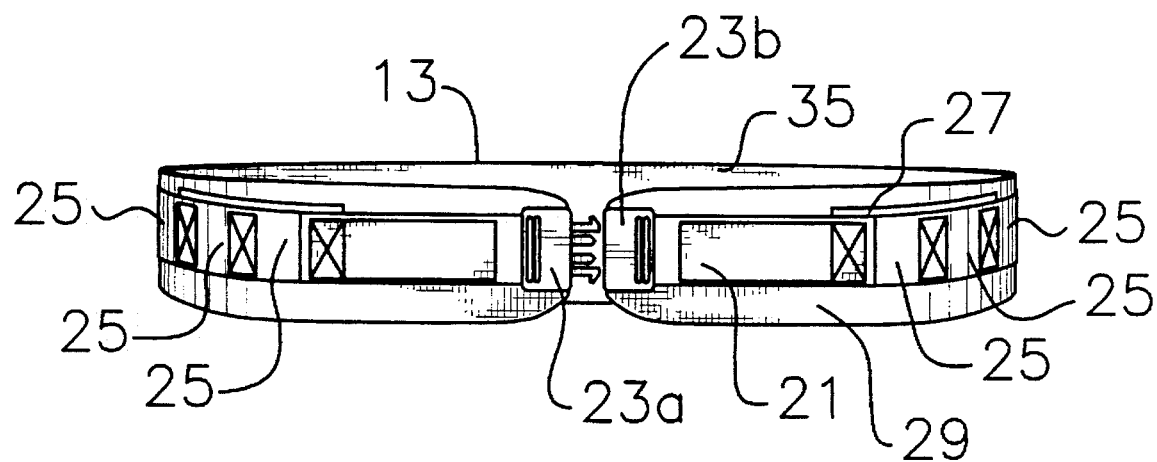
FIG. 2 is a perspective of the present invention showing the support belt.
Figure 3:
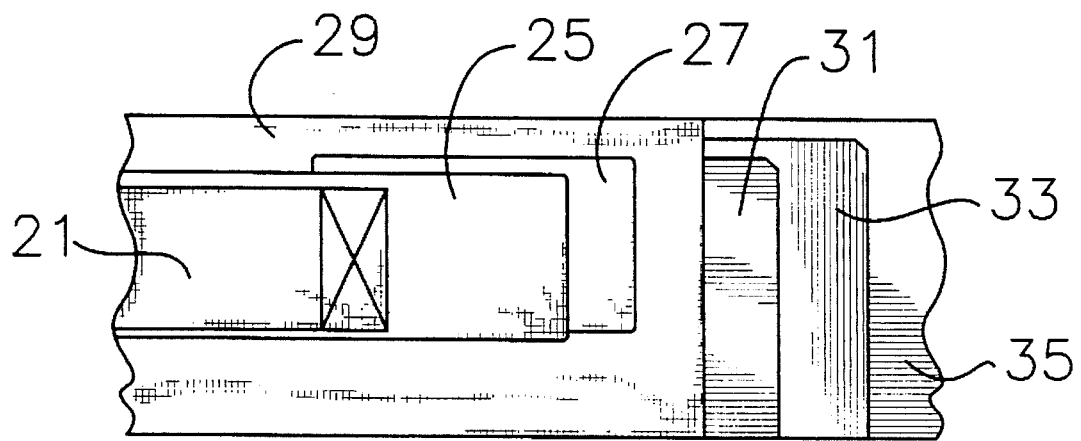
FIG. 3 is a section of the support belt of the present invention.

Referring specifically to FIG. 2 and FIG. 3, support belt assembly 13 is multilayered and may be made as follows in order to comfortably support and distribute the upper body weight to the pelvic area. Belt 21 is the outer belt which provides strength and is made of nylon or other material which can support the load imparted from the support tube assemblies 15. Belt 21 is adjustable about the pelvis of the user with buckle 23. Buckle 23 can be made of two inter-connecting parts, 23a and 23b, which allows the belt 21 to be easily buckled or removed while maintaining the adjusted length. The buckle 23 may be made of a hard plastic like material, metal, or some other composite. The belt 21 and buckle 23 must be strong enough to withstand strong lateral and longitudinal forces. The free end of belt 21 may be secured by VELCRO material.

Pockets 25 will be formed on both sides of the support belt assembly 13 by stitching belt 21, as shown, to the underlying layers. Pockets 25 sustain tube assembly 15 and are, therefore, the main load bearing part of the support belt assembly 13. There will be a strip 27 which serves as the inside half of the pocket 25. The pocket 25 can also be formed with strip 27 on the outside of belt 21. Strip 27 can be made of the same material as belt 21. In the alternative the support pocket may be made by sewing the belt 21 directly to the underlying layers of support belt assembly 13. Layer 29 lies beneath belt 21 and strip 27 and is also an outer layer of the support belt assembly 13. Layer 29 is made of nylon, polyester, Naugahyde, or similar material. Beneath outer layer 29 is an intermediate layer 31 comprising a bumper of hard rubber, semi-flexible plastic, or other suitable material, which would absorb and distribute the shock or pressure exerted by the support tube assembly 15. Beneath layer 31 is a thicker layer 33 of foam rubber, or other padding type substance, which absorbs the pressure transmitted from layer 31 and forms a cushioning pad which can contour to the user's body. Layer 35 is the inner layer of the belt assembly. Layer 35 is made of nylon, polyester, naugahyde, or similar material which will also contour to the user's body. Layer 35 will also be such that it will not easily slip, will not be affected by moisture, and will be strong enough to support the thread which forms pockets 25 and which holds belt 21 in place. The construction of the support belt assembly 13 allows it to be tightly secured without causing discomfort, accordingly, the belt 13 can be worn, and used, without the support tube assemblies 15. As can be seen, the multilayered construction of the belt 13 allows for the distribution of forces imparted by the biasing means about the user.

The pockets 25 allow for lateral adjustment in order that tube assembly 15 can be located directly under the arms, or in a position which best suits the requirements or exercise needs of the user. Placement of support tube assemblies 15 forward or rear of the users underarm can cause a posterior or anterior tilt to the pelvis which is preferable for treating certain conditions. The adjustment also allows individuals with basically the same waist and hip size but with different body configurations to use the same size belt. It also allows for body changes of an individual user.

Figure 4:
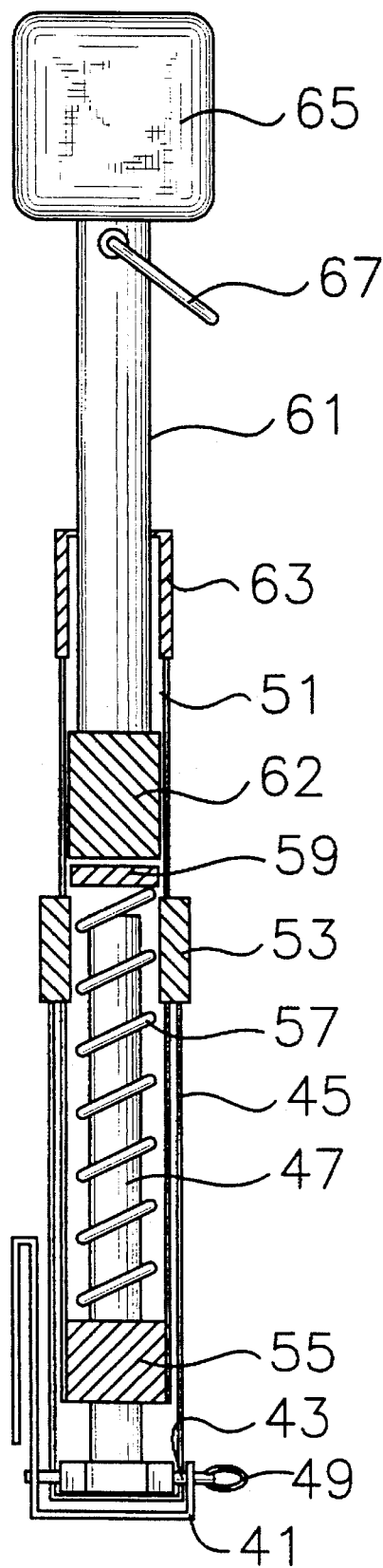
FIG. 4 illustrates the biasing mechanism.
Figure 5:
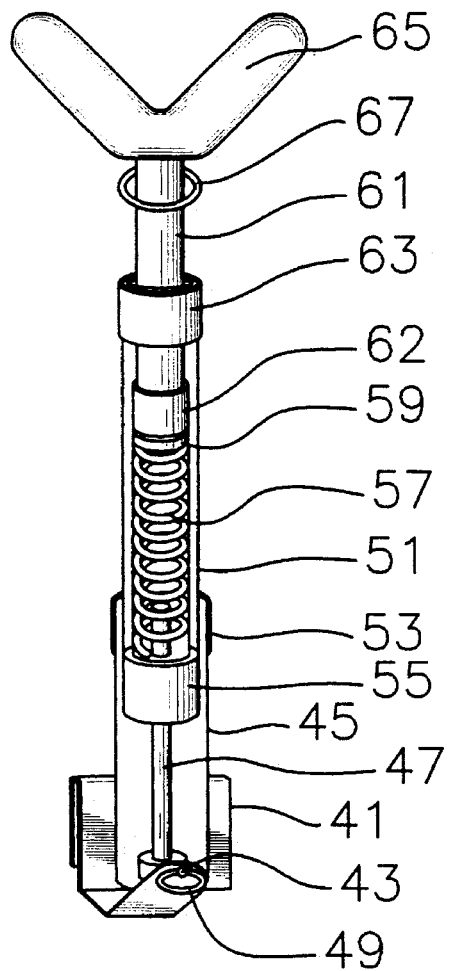
FIG. 5 illustrates the biasing mechanism.

Referring now to FIG. 4 and FIG. 5, clip/bracket 41, which is made a part of support tube assembly 15, allows the assembly to be easily attached or removed. The clip/bracket 41 will attach to pocket 25, one on each side of the user. The clip/bracket 41 may be made of steel (preferably stainless or spring steel) or other strong metal or material which is capable of supporting and transferring the weight imparted through the support tube assembly 15 to support belt assembly 13. Pin 43 connects clip/bracket 41 to lower tube 45 and adjustment bolt 47. Pin 43 has a head on one end and a hole on the outer end. Ring 49 goes through the hole on the outer end of pin 43 to secure pin 43 in the clip/bracket 41. In the alternative, pin 43 and ring 49 can be replaced by a rivet. As shown, lower tube 45 houses adjustment bolt 47, which is threaded. Tube 45 also encases the lower part of adjustment tube 51. The upper part of tube 45 serves to brace adjustment tube 51. Rubber sleeve 53 fits on the top of tube 45. Sleeve 53 prevents tube 51 from errantly turning as a result of vibration or other causes.

In the preferred embodiment the lower part of adjustment tube 51 is solid and threaded to form a nut 55 which accommodates adjustment bolt 47. In the alternative, the lower part of adjustment tube 51 can be fitted with an anchor nut which would accommodate adjustment bolt 47. As a result of the cooperation of adjustment bolt 47 and nut 55, the tube assembly 15 is longitudinally adjustable by turning adjustment tube 51. This action causes the support tube assembly 15 to expand or contract depending on the direction tube 51 is turned. The amount of upward force, lift, tension, or pressure is, therefore, varied by turning adjustment tube 51. This adjustment means also allows the support tube assembly 15 to accommodate wearers of different height and body configurations. In the alternative the inside of lower tube 45 and the outside bottom part of adjustment tube 51 could be threaded. The threads on the two tubes would cooperate and allow length adjustment of the tube assembly 15. In another alternative, the lower tube 45 would have a number of vertical holes which would accommodate a spring loaded button in the adjustment tube. The length of the apparatus would be raised or lowered by pressing in the adjustment button and raising or lowering the tube to another hole. This method, however, would not offer the infinite settings of the preferred embodiment, nor would it be as easy to adjust.

The adjustment tube 51 contains a compression spring 57 or other similar biasing means. The spring 57 rests on the solid part of tube 51 which forms nut 55, or in the alternative on the fitted nut. Springs with different compression ratios are interchangeable to allow for, not only, different body weights and configurations, but also for the particular requirements, or needs, of the user. Greater arm strength and muscle strength might also eventually result in a need to increase the amount of support or resistance.

The adjustment bolt 47 rests untouched in the middle of compression spring 57. Also, compressing spring 57 does not cause it to encounter, or experience interference from, adjustment bolt 47. There may be a washer 59 with a center hole which separates spring 57 and compression tube 61. The center hole in washer 59 also allows penetration of bolt 47 without interference. The lower part of compression tube 61 is fitted with a nylon or other type bearing 62 and remains and operates in adjustment tube 51. During operation, bolt 47 does not interfere with compression tube 61. Adjustment tube 51 has a removable sleeve/bearing 63, made of nylon or other friction reducing material, at the top to prevent the assembly from errantly coming apart. Sleeve/bearing 63 also serves to brace, and minimize friction from, compression tube 61.

A padded underarm rest or support means 65 is mounted atop compression tube 61. The underarm rest 65 is preferably V shaped in order to allow greater underarm pressure without affecting the nerves and blood vessels of the arms. In the alternative the underarm rests could be straight or curved. The padding for the underarm rest is foam rubber or other suitable weight distributing material.

Just below armrest 65 is a ring 67 which is secured to compression tube 61. Ring 67 is used for attachment of handle assembly 17.

Figure 6:
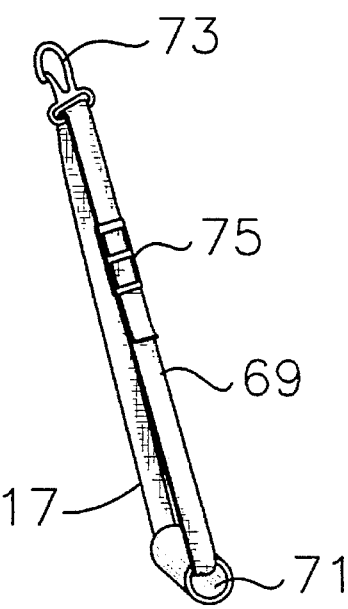
FIG. 6 illustrates the detachable handle assembly.

Referring now to FIG. 6, which shows the handle assembly 17. Handle assembly 17 can be used to ease the pressure on the underarm, cause greater decompression and unloading by allowing increased force to the biasing means, and/or for conducting different types of exercises. The handle assembly 17 or other transfer means also allows the device to function by giving maximum effect for transferring the load or pressure exerted by the biasing means away from the support means. Strap 69 is preferably a ½ inch to ¾ inch strap of nylon but may be of any suitable material. A rigid rod or tube could be used to replace strap 69. Strap 69 may be threaded through the handle 71, or, in the alternative, coupled to a shaped metal rod which would connect handle 71 to strap 69. Strap 69 is also threaded through clip 73, which may be spring loaded for easy attachment and removal. A buckle 75 connects the ends of strap 69. The buckle 75 also enables length adjustments for strap 69 which allows for different needs and/or exercise requirements and different body configurations.

Figure 7:
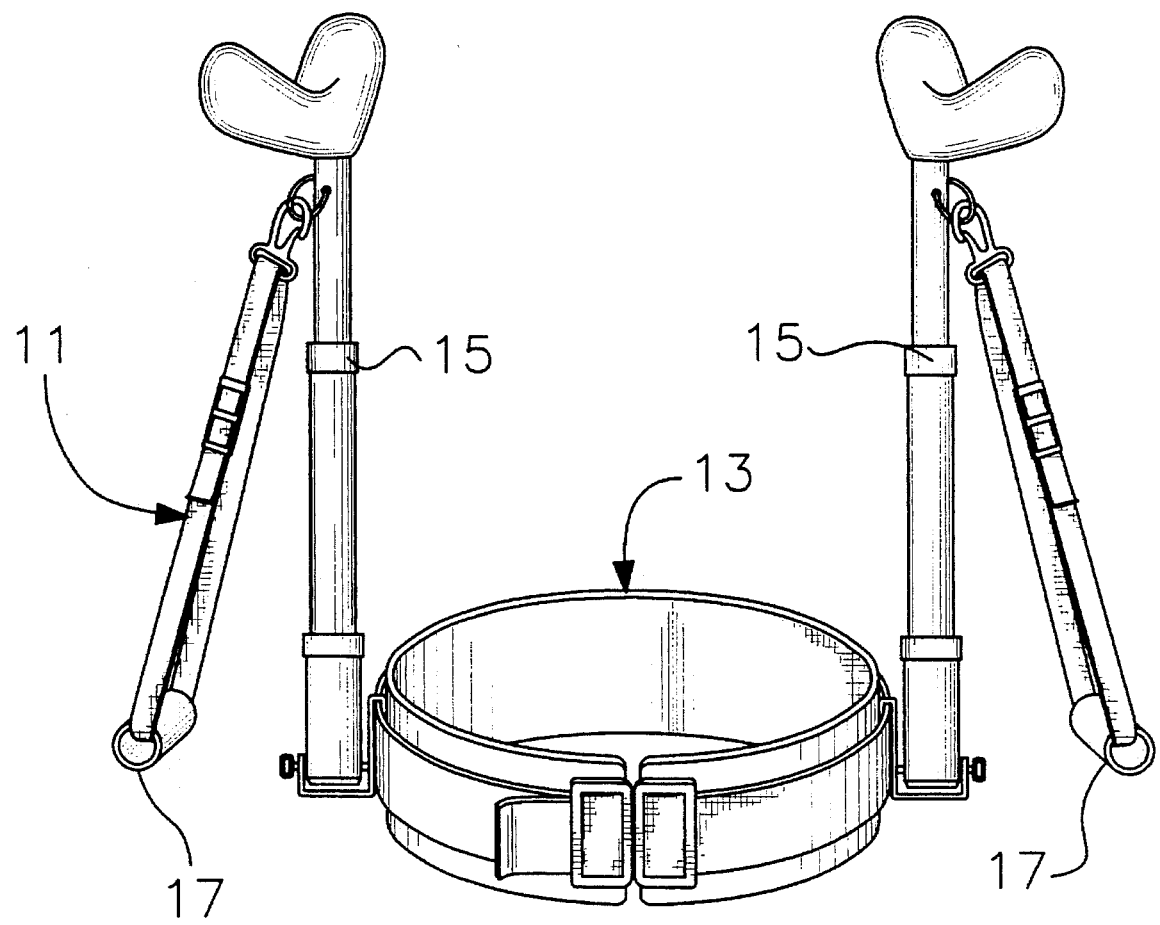
FIG. 7 is a perspective of the present invention with the straps free to cause lift from straightening the arms.

The configuration shown in FIG. 7 allows for greater arm flexion. This configuration, with the length of the handle assembly 17 shortened, allows for more arm involvement and, therefore, greater decompression and unloading of the middle and lower spine. It provides for extreme stretching of the muscles in the upper body which affect the spine. This configuration also allows for greater stretching and exercising of the muscles which affect appearance, i.e., the rectus abdominus (the outer stomach muscles) and the external obliques ("love handles").

Figure 8:
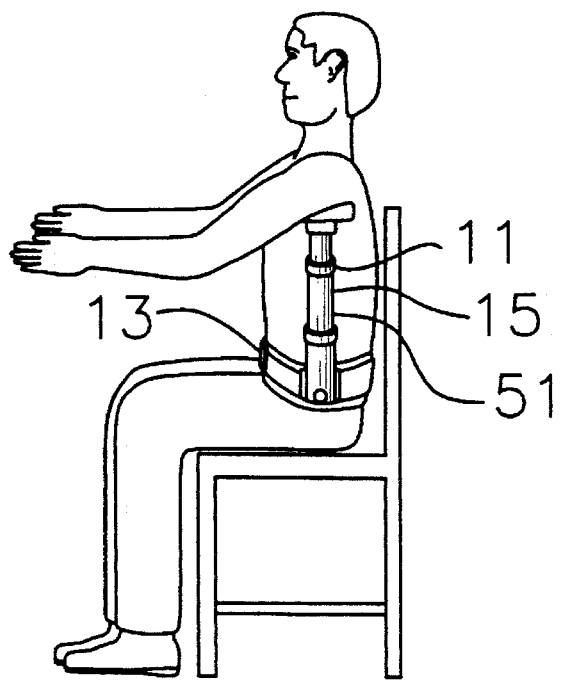
FIG. 8 depicts an embodiment of the invention without the detachable handle assembly while the wearer is seated.
Figure 9:
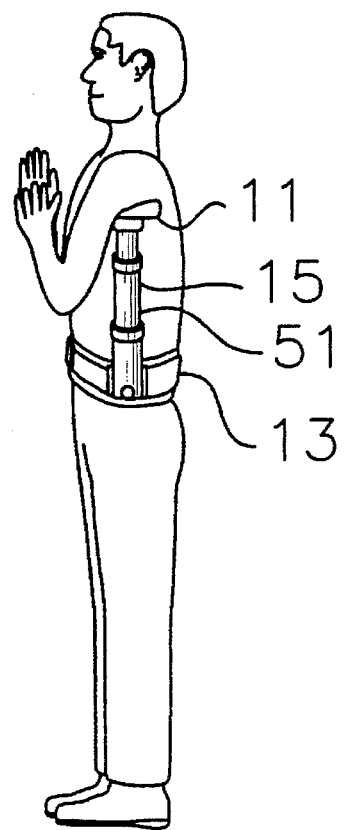
FIG. 9 depicts an embodiment of the invention without the detachable handle assembly while the wearer is standing.

The invention, may, therefore be defined in terms of passive and active utilization:

When used passively without the handle assembly 17 the invention 11, as shown in FIG. 8 and FIG. 9 depicts examples showing the wearer seated and standing, provides basic spinal traction, unloading, and decompression. Compressive stresses on the wearer's thoracic and lumbar regions of the spine are minimized as a result of weight from the upper part of the wearer's body being transferred through tube assembly 15 to belt assembly 13 which distributes the weight to the pelvic region. The invention 11, in the passive mode, in effect provides an exterior support means which supplements and unloads the spine. The system supports the back for a wearer who has suffered some back injury or has some back defect. By utilizing the traction system and traction method of the instant invention, the wearer, with his arms free, is able to walk, sit, lay, stand, etc. Moreover, the system is readily adjustable, by rotation of adjustment tube 51, to increase or decrease the degree of lift and traction. The wearer can instantly increase the amount of traction with the shoulder muscles by simply lowering the shoulders down towards their normal position. This causes increased upward pressure, or resistance, from the biasing means in the support tube assembly 15. Alternately, the wearer can instantly decrease the amount of traction by simply raising the arms. When used passively, the invention 11 also has the additional advantage of absorbing vertical impacts or shocks to the spine and can, therefore, minimize or eliminate pain which would otherwise result. The present invention may also minimize or eliminate pain due to spinal ailments while the spine recuperates from previous injuries.

Figure 10:
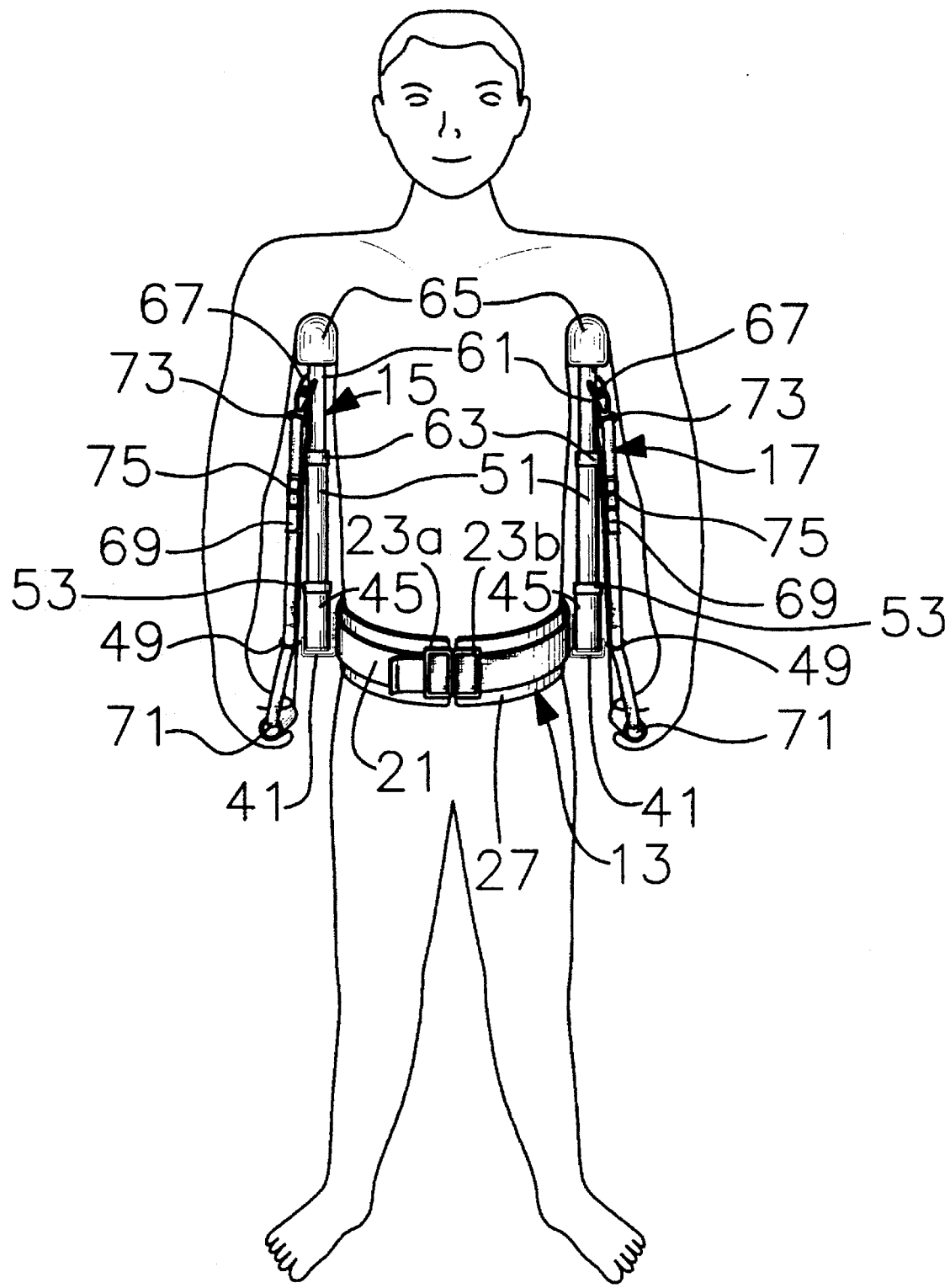
FIG. 10 is a perspective of the present invention shown in operative connection with the straps through the bracket rings to cause lift from the shoulders by holding handles with the arms straight and rigid.

In the embodiment shown in FIG. 10 the clip 73, and strap 69 are first threaded through ring 49, before the clip 73 is attached to ring 67. This configuration, with the strap 69 lengthened, forces the arms to remain straight and rigid. This results in less involvement of the arms, more involvement of the shoulders, and assures a straight line of force. This transfers most of the load from the underarms to the hands and forces primarily the muscles of the shoulders to oppose the biasing means. This configuration works best for stretching the muscles of the neck and upper spine. This embodiment also serves to secure the handle attachment 17 when they are not being used.

When used actively with the handle assembly 17, the present invention allows greater decompression forces to the spine and exercise of numerous muscles in the upper body. In the active mode, the user would adjust the length of the support tube assembly 15, and the handle assembly 17, to accomplish the results desired. The adjustment of support tube assembly 15 would raise the shoulders above their normal position which induces traction. Increased spinal decompression is accomplished by lowering the shoulders against the biasing means. Exercise is accomplished by repeatedly forcing the shoulders down into their normal position against the resistance of the biasing means and then allowing the biasing means to raise the shoulders.

In the active mode, the present invention pays particular attention to the cervical, thoracic, and lumbo-sacral regions of the spine and the muscles which support the spine. It stretches and exercises the muscles of the neck and upper body while decompressing the thoracic and lumbo-sacral regions of the spine in order to provide relief from back pain. The present invention also offers prevention of pain and injury from back maladies by elasticizing and strengthening the muscles related to the spine; this includes the back support muscles, spinal erectors, stomach muscles, (abdominals) etc. The present invention, by exercising the muscles of the upper body in accomplishing it's primary objective, also tones, and reduces fat in, the upper body. This is important since excess stomach weight is one of the primary causes of back pain. The present invention accomplishes the results listed herein as well as numerous benefits not listed.

Figure 11:
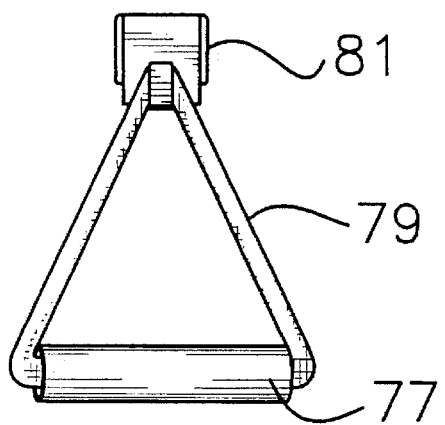
FIG. 11 illustrates an exercise accessory that incorporates a handle, stretchable resistance medium, and a belt clip bracket.

FIG. 11 illustrates an accessory which incorporates a handle 77, a stretch means 79 which can be rubber, elastic material, or expansion springs, and a belt clip bracket 81 which would connect to clip/bracket support pocket 25 shown in FIG. 2 and FIG. 3. This would allow the user to exercise with the apparatus without the support tube assemblies 15 or the handle assembly 17. This configuration would not allow the continuous lift between exercise strokes afforded by the support tube assemblies 15 and would not allow for variable resistance adjustments without changing the stretch means 79. It would, however, provide cyclic traction and decompression and would provide exercise within the scope of the invention.

Figure 12:
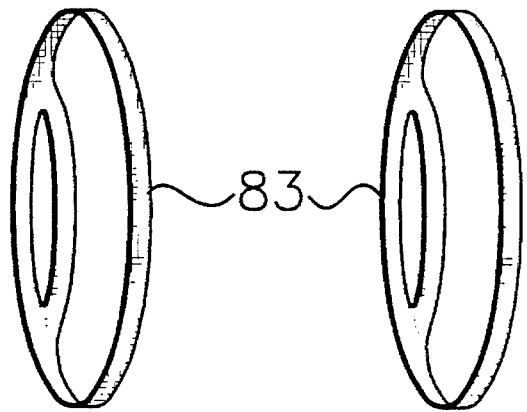
FIG. 12 illustrates accessory straps that would allow the user to secure the underarm pad to the shoulders.

FIG. 12 shows elastic accessory straps 83 which could be used to secure the underarm pads to the arms or shoulders.

Figure 13:
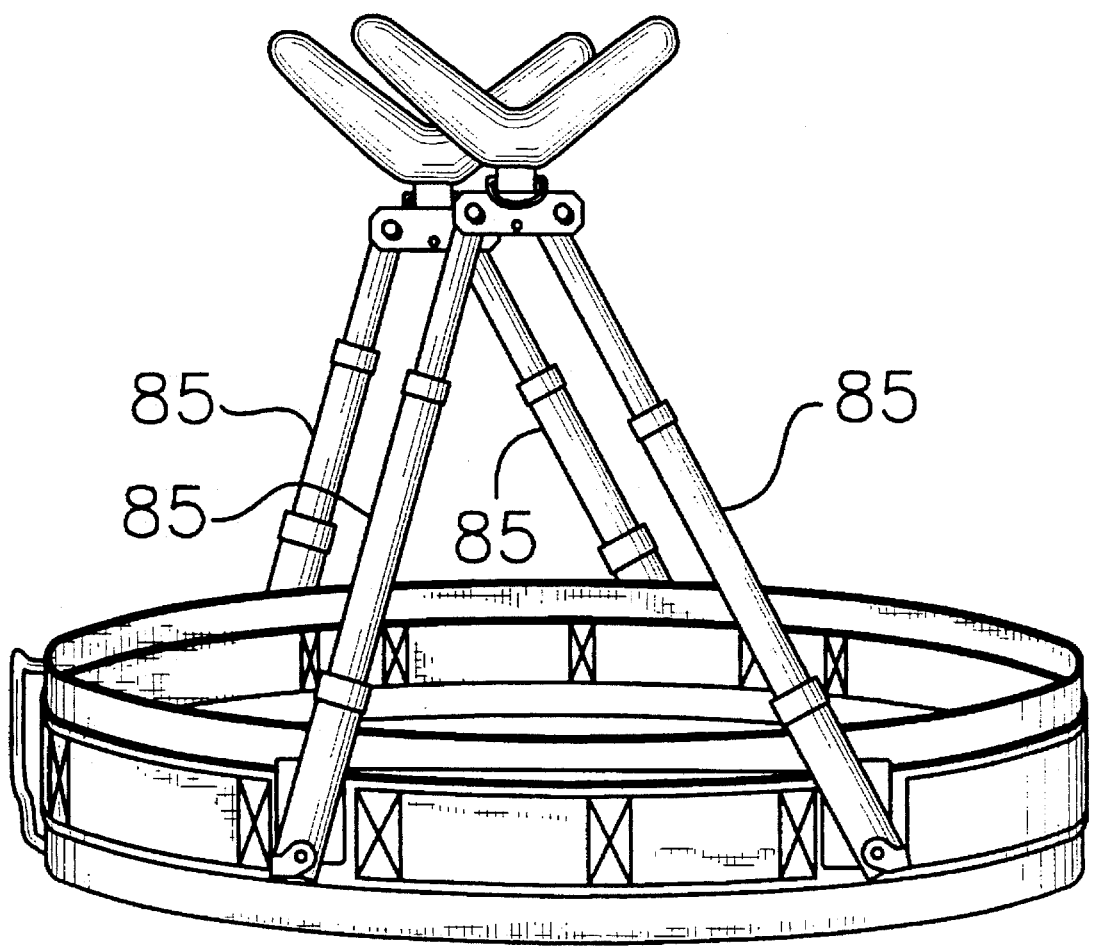
FIG. 13 is an alternate embodiment utilizing two (2) support tube assemblies on each side to restrict flexion and rotation.

FIG. 13 shows an alternate embodiment of the present invention which would incorporate two support tubes 85 on each side of the user which when needed would restrict upper body flexion and rotation. This embodiment would rely on triangulation which would restrict bending and turning but would allow traction, decompression, unloading, stretching, and exercising in a straight line of force.

Another variation would allow two or more parallel support tubes on both sides of the user, which would not affect upper body flexion and rotation, in order to accommodate extremely large or strong users.

Figure 14:
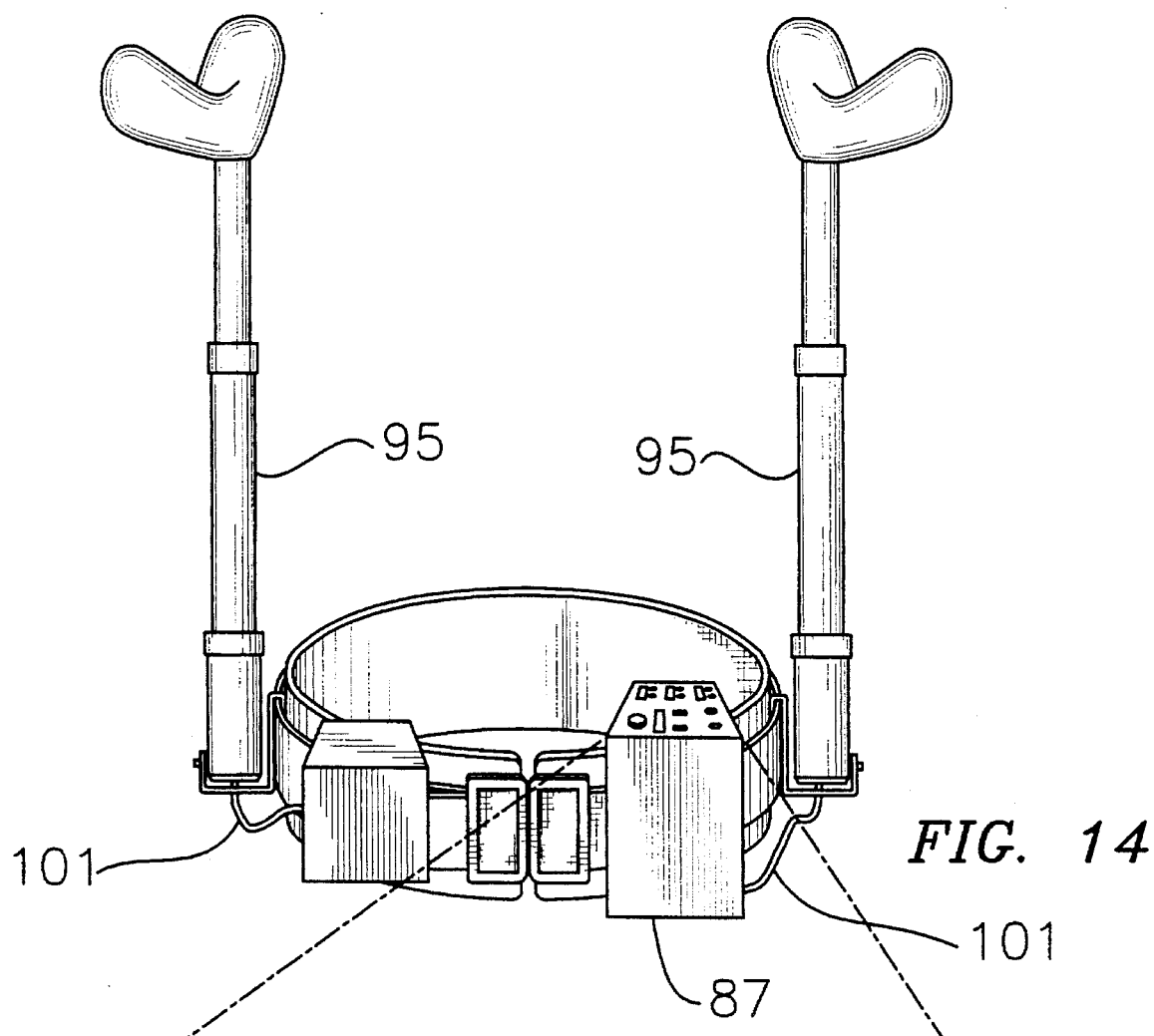
FIG. 14 illustrates a modification utilizing automation and outside forces to accomplish traction and decompression.
Figure 15:
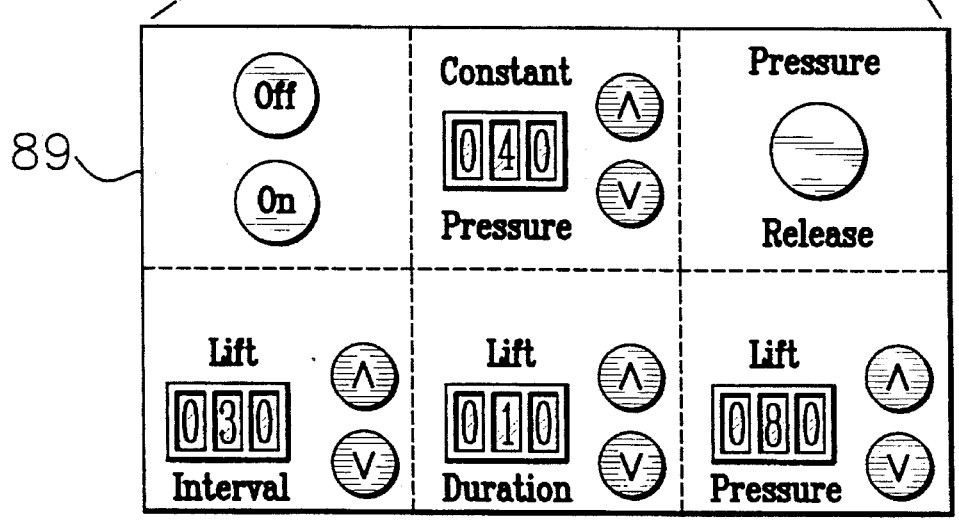
FIG. 15 is an exploded view of the control panel from the automated version shown in FIG. 14.
Figure 16:
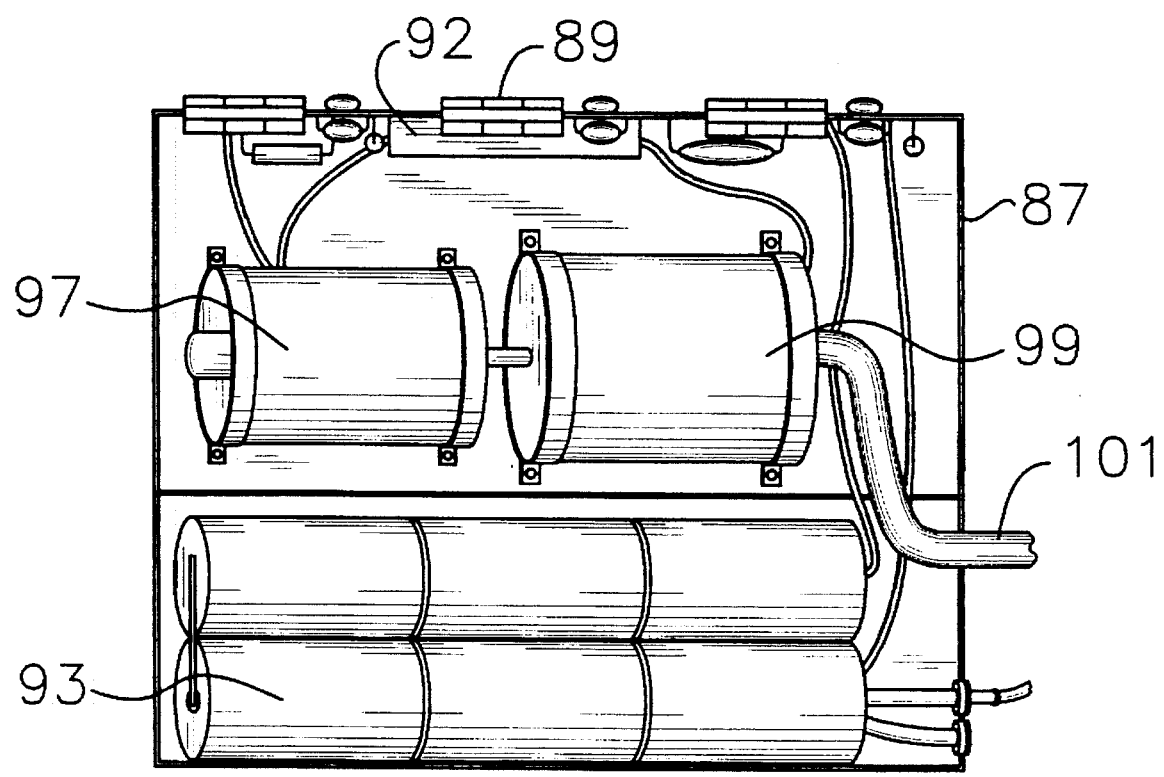
FIG. 16 is an internal view of the automated control box.

FIG. 14, FIG. 15, and FIG. 16, depict an alternate embodiment utilizing automation to allow the user to automatically vary the tension from the biasing means. This embodiment would allow the user to accomplish spinal traction and decompression with minimal user involvement. A control box 87 would contain a control panel 89 which utilizes microprocessors and a CPU 91, a rechargeable battery 93, and a system which would cause lift from the support tubes 95. The lift system could rely on pressure from an electric motor 97 and a pump 99 (pneumatic, hydraulics, etc.). In the alternative, the lift system could rely on a magnetic or other electrical system which would cause separation of and, therefore, lift from the support tubes. The control panel 89 would regulate the amount of continuous lift, the intervals between extreme lift, and the duration of extreme lift. In addition to on and off buttons it would have a pressure relief button. This version could operate on AC or DC power. The control box 87 could also utilize a battery pack 92 for extended portable use. Pressure line 101 would extend from the pump 99 to the support tubes 95. The pressure applied to support tubes 95 would cause them to expand longitudinally. The automated embodiment of the present invention would be ideal for users who could not easily use their arm or shoulder strength to accomplish many of the objectives of the present invention.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

What is claimed is:

1. A multipurpose apparatus for applying spinal traction, distraction, manipulation, and adjustment, for exercising, and for stretching muscles, tendons, and ligaments of the upper body comprising:

(a) a belt means for providing support above the hips and pelvis of the user;

(b) a first telescopic support means mounted from each side of said belt means;

(c) a biasing means mounted inside said first telescopic support means for exerting upward pressure;

(d) a second support means mounted on an end of each said first telescopic support means distal from said belt means for supporting the user under the arms against the pressure of said biasing means;

(e) a transfer means connected to said first telescopic support means for transferring the pressure exerted by said biasing means away from said second support means, wherein said transfer means further comprises a flexible strap means attached to said first telescopic support means at a proximal and of said strap means, said strap means further comprising a grip means on the distal end from said first telescopic support means whereby the user can exert muscle tension against said biasing means by grasping said grip means with his hands and pulling said strap means downward away from said second support means thereby pulling said second support means away from the user's underarm region and reducing the tension of said biasing means felt by the user in that underarm region, 2. The apparatus of claim 1 wherein said transfer means further comprises a handle for grasping by the user attached to said strap means being adjustable in length.

3. The apparatus of claim 1 wherein said belt means is adjustable to fit about the hips and pelvis of the user.

4. The apparatus of claim 3 wherein said adjustable belt means is multilayered to distribute the forces imparted by said biasing means about the user.

5. The apparatus of claim 1 wherein said second support means further comprises a padded support under the arms of the user attached to said biasing means.

6. The apparatus of claim 1 wherein said biasing means further comprises an adjustment means for adjusting the distance between said belt means and said second support means.

7. The apparatus of claim 1 wherein said biasing means further comprises an adjusting means for adjusting the amount of force exerted between said second support means and said belt means.

* * * * *